United States Patent [19]

Nichols

[11] 4,330,253

[45] May 18, 1982

[54] COMPOSITE DIE FOR FORMING A PLUNGER FOR USE IN A SHUTOFF VALVE FOR A MEDICAL SUCTION APPARATUS

[76] Inventor: Robert L. Nichols, 808 Ft. Worth St., Jacksonville, Tex. 75766

[21] Appl. No.: 187,073

[22] Filed: Sep. 15, 1980

Related U.S. Application Data

[60] Division of Ser. No. 923,397, Jul. 10, 1978, Pat. No. 4,256,109, which is a continuation-in-part of Ser. No. 923,346, Jul. 10, 1978, Pat. No. 4,245,637.

[51] Int. Cl.³ ............................................. B29C 7/00
[52] U.S. Cl. ................................. 425/437; 249/66 A; 425/DIG. 58; 425/556
[58] Field of Search ............... 425/437, 556, 566, 542, 425/805, DIG. 58; 249/66 A, 160

[56] References Cited

U.S. PATENT DOCUMENTS

| | | | |
|---|---|---|---|
| 3,020,594 | 2/1962 | Makowski | 425/DIG. 58 |
| 3,357,058 | 12/1967 | Kritik | 425/805 |
| 3,373,460 | 3/1968 | Lodney | 425/DIG. 58 |
| 3,591,898 | 7/1971 | Stenmo | 425/556 |
| 4,125,246 | 11/1978 | von Holdt | 249/160 X |
| 4,155,698 | 5/1979 | Aichinger | 425/556 |

FOREIGN PATENT DOCUMENTS 1006373 9/1965 United Kingdom ............... 425/556

OTHER PUBLICATIONS

"Effective Mold Design", Article in *Plastics Engineering*, 1958, pp. 111–115.

Primary Examiner—J. Howard Flint, Jr.
Attorney, Agent, or Firm—Richards, Harris & Medlock

[57] ABSTRACT

The specification discloses an improved shut off valve for a canister and lid assembly used as part of a medical suction apparatus. The valve includes a cylindrical plunger made of a soft rubber-like material and having an upwardly facing concave disc integrally formed on the top of the plunger. When the fluid within the canister rises to a predetermined level, the plunger floats upwardly forcing the disc into a sealing relationship covering and blocking a suction port. Alternately, the soft rubber plunger may be dimensioned for use as a plunger cap for the upper end of a hard plastic plunger.

The soft rubber plunger and integral concave disc are formed in a composite die, including a disc die and a plunger die. Rubber is injected into the composite die through a bore to form the plunger and integral concave disc. To remove the rubber concave disc from the disc die, air is injected into a bore while the disc die is simultaneously moved away from the plunger die.

1 Claim, 6 Drawing Figures

COMPOSITE DIE FOR FORMING A PLUNGER FOR USE IN A SHUTOFF VALVE FOR A MEDICAL SUCTION APPARATUS

CROSS-REFERENCE TO RELATED APPLICATIONS

The present application is a divisional of application Ser. No. 923,397, filed July 10, 1978 by Robert L. Nichols, now U.S. Pat. No. 4,256,109, issued Mar. 17, 1981 and entitled SHUTOFF VALVE FOR MEDICAL SUCTION APPARATUS, which case was a continuation-in-part of application Ser. No. 923,346, filed July 10, 1978 by Robert L. Nichols, now U.S. Pat. No. 4,245,637, issued Jan. 20, 1981 and entitled SHUTOFF VALVE SLEEVE.

FIELD OF INVENTION

The present invention relates to a composite die, and more particularly relates to a composite die for forming an integral plunger for use with a float system in a medical suction apparatus.

BACKGROUND OF THE INVENTION

Conventional medical suction apparatus have included canister and lid assemblies with a suction port and a patient port, each extending through the lid. Typically, a vacuum pump is connected to the suction port, and a tube is connected between the patient and the patient port. The suction of the vacuum pump is then transmitted through the suction port, through the canister and through the patient port to withdraw fluids from the patient during a medical procedure. The fluid enters the canister through the patient port. When the fluid rises to a predetermined level, a shut off valve blocks the suction port eliminating the suction at the patient port and preventing additional fluid from being withdrawn from the patient.

Shut off valves used in such medical suction apparatus are known to have included plungers connected to a float for moving upwardly in response to the rising fluid level within the canister to block the suction port. One type of plunger previously used included an inwardly tapered upper end. When the fluid within the canister rose to a predetermined level, the tapered end of the plunger moved upwardly and was forced into the suction port to block or shut off the suction. This type of plunger suffered from a misalignment problem. If the suction port and the plunger were out of alignment, it was possible that the plunger would engage other lid structure, and the tapered portion of the plunger would not be inserted into the suction port. In such event, the suction port would not be sealed, and fluid would continue to be withdrawn from the patient until the canister overflowed. Also, this type of plunger was associated with a problem of foreign material becoming lodged between the tapered end of the plunger and the suction port. The foreign material would prevent proper sealing of the plunger against the suction port, and, again, the medical suction apparatus would continue to function until the canister was overflowing.

Another type of plunger known to have been used in a shut off valve for a medical suction apparatus included a float connected to a hard plastic plunger having a small plastic post extending upwardly from the upper end of the plunger. Typically, the upper end of the post included an enlarged head or retainer ring, and a rubber disc having a small aperture at its center was mounted on the post by deforming the disc to insert the post into the aperture. The deformation of the disc when mounted on the post caused the disc to form an upwardly facing suction cup. When the plunger was forced upwardly by rising fluid in the canister, the rubber disc covered and blocked the suction port. In the use of this type of plunger and cup assembly, leakage was found to occasionally occur between the post and the rubber disc. This problem necessitated testing each valve to insure proper functioning. Also, an excessive amount of hand labor was required to deform and place the disc on the post.

Thus, a need has arisen for a shut off valve employing a suction cup to block the suction port that may be manufactured with reduced hand labor. Also, a need has arisen for a plunger and suction cup assembly that combines the economies of manufacturing by molding with the effectiveness of a suction cup shut off valve. Furthermore, a need has arisen for a suction cup and plunger for use in a shut off valve that reliably provides a nonleaking seal covering the shut off port such that individual testing of each valve will not be necessary and that may be used without a separate float, if desired.

In accordance with the present invention, a composite die is provided for forming a flexible plunger having an upwardly facing concave disc formed on the top of the plunger. The composite mold includes a plunger die having a generally annular cylindrical cavity formed therein and a disc die for being positioned above the plunger die to form the composite die. The disc die includes an upwardly facing, concave, disc shaped cavity with an opening formed at the center of the disc shaped cavity extending through the lower surface of the disc die positioned over the center end of the annular cavity in the plunger die. A bore extends from the center of the disc shaped cavity to the upper surface of the disc die for injecting rubber into the composite die and for injecting air into the disc die to facilitate removal of the rubber disc formed in the disc shaped cavity.

BRIEF DESCRIPTION OF THE DRAWING

The advantages of the present invention will best be appreciated by those of ordinary skill in the art by reference to the following detailed description when considered in conjunction with the accompanying drawings in which: p

DETAILED DESCRIPTION OF THE INVENTION

Figure 1:
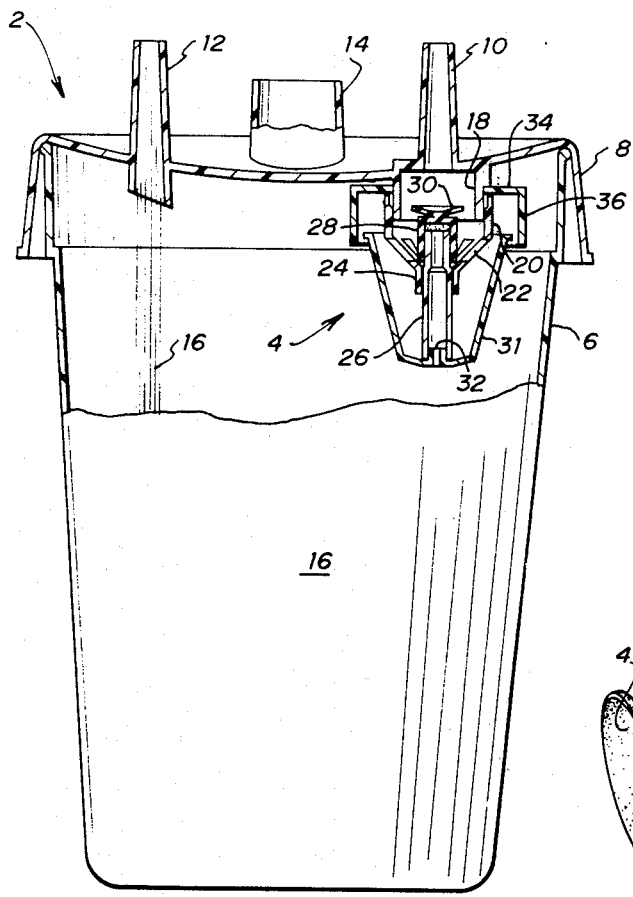
FIG. 1 is a somewhat diagrammatical cross section of a canister and lid assembly with a shut off valve depending below the lid.

Referring now to FIG. 1, there is shown a somewhat diagrammatical cross section of a canister and lid assembly 2 having a shut off valve 4 embodying the present invention. The canister and lid assembly 2 includes a canister 6 and a lid 8 sealably covering the canister. A suction port 10 and a patient port 12 are formed in the lid 8 communicating between the interior and exterior of the canister 6 covered by the lid 8. A spout 14 is also formed on the lid 8 for use in emptying fluids from the canister 6.

In operation, the spout 14 is sealed with a cap, and a vacuum pump is attached to the suction port 10. A tube or suction line is then connected between the patient port 12 and a patient. A suction is applied through suction port 10, and a vacuum is created inside canister 6 that, in turn, creates a suction at patient port 12. During a medical procedure, the suction at patient port 12 is operable to withdraw fluid 16 from the patient and into the canister 6.

In FIG. 1, the shut off valve 4 depends from a cylinder 18 extending downwardly from the interior surface of lid 8. A clamping cylinder 20 frictionally clamps over the cylinder 18, and a plurality of fingers 22 extend downwardly and inwardly from the clamping cylinder 20 to support a vertically oriented plunger guide 24. A rigid plunger 26, preferably constructed from a hard plastic, is disposed for sliding motion within the plunger guide 24.

The plunger 26 is cylindrical and the top of the plunger is covered by a soft flexible plunger cap 28. An upwardly facing concave disc 30 is integrally formed on the top of the plunger cap 28, and both the plunger cap 28 and disc 30 are formed from a soft, flexible, resilient material such as a silicone rubber. While the plunger 26 is dimensioned for free sliding movement inside the plunger guide 24, the diameter of the plunger cap 28 is sufficiently large to prevent the cap 28 from passing through the plunger guide 24. Thus, the plunger cap 28 will limit the downward sliding motion of plunger 26. The plunger cap 28 is sufficiently elastic to firmly grasp the plunger 26 with sufficient force to prevent the plunger 26 from being withdrawn from the cap by loads normally placed on the plunger 26.

A float 31 is attached to the lower end of the plunger 26 by means of a prong 32 extending upwardly from the bottom of float 31. The prong 32 is inserted into the lower end of the plunger 26 for frictional engagement with the inner walls thereof sufficient to support the weight of float 31. In this manner, the plunger cap 28 rests on the plunger guide 24 to support the plunger 26 and the float 31.

Still referring to FIG. 1, a hub 34 extends outwardly from the upper end of cylinder 18, and a cylindrical wall structure 36 downwardly depends from the hub 34. The wall structure 36 partially encompasses the float 31 and provides a tortuous path for air entering the suction port 10 to prevent direct migration of fluid and aerosol particles into the suction port 10. In order to pass from inside the canister 6 into the suction port 10, air must first travel upwardly between the wall structure 36 and the upper end of the float 31; then the air passes downwardly between the upper end of float 31 and the clamping cylinder 20; finally, the air passes between the fingers 22 and upwardly into the suction port 10.

Figure 2:
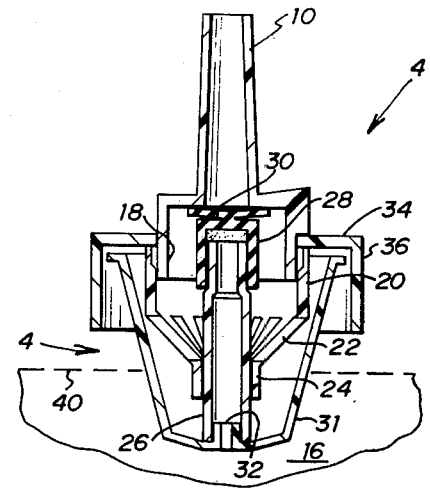
FIG. 2 is a cross section of the shut off valve and suction port shown in FIG. 1.

Referring now to FIG. 2, there is shown a cross section of the shut off valve 4 and the suction port 10. In this view, the shut off valve 4 is shown in position as it would appear when the fluid within canister 6 has risen to a predetermined level generally indicated by dotted line 40. The float 31 has risen in the fluid 16 forcing the plunger 26 upwardly in a sliding motion through the plunger guide 24. The disc 30 mounted on the top of plunger 26 is forced against the suction port 10 in a sealed relationship for covering and blocking the suction port. Thus, when fluid 16 rises to the predetermined level of line 40, the shut off valve 4 is operable to block the suction port 10. Referring to FIGS. 1 and 2, it will be appreciated that the blockage of the suction port 10 by the shut off valve 4 will prevent a vacuum from being formed within canister 6, and the fluid 16 will cease to enter the canister 6 through the patient port 12.

The plunger cap 28 and the integrally formed disc 30 is an important feature of the invention. As will be hereinafter described in more detail, the plunger cap 28 and disc 30 may be manufactured by inexpensive and efficient injection molding techniques. Also, the cap 28 is easy to mount on plunger 26 with a minimum amount of hand labor, and the disc 30 forms a reliable seal on suction port 10 without a leakage problem.

Figure 3:
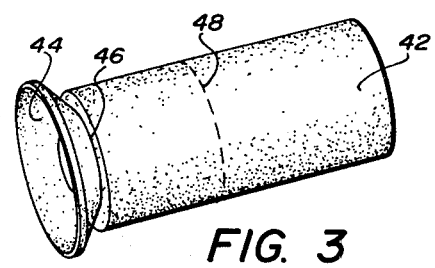
FIG. 3 is a perspective view of a soft flexible plunger having a concave disc integrally formed on one end of the plunger.

Referring now to FIG. 3, there is shown a view of a soft rubber plunger 42 with a concave disc 44 integrally formed on one end of the plunger 42. The center region 46 of the disc 44 is connected to the center of one end of the plunger 42. By cutting the plunger 42 along the dotted line 48, the plunger 42 may be used as a plunger cap, such as plunger cap 28 illustrated in FIGS. 1 and 2.

Figure 4:
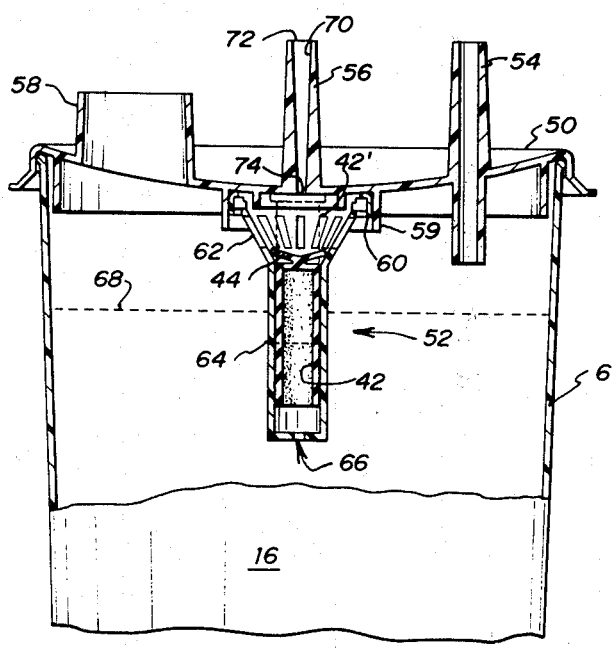
FIG. 4 is a somewhat diagrammatical cross section of a lid for a canister and a shut off valve utilizing an embodiment of the present invention.

Referring now to FIG. 4, there is shown a somewhat diagrammatical cross section of a canister lid 50 and a shut off valve 52 utilizing the plunger 42. Canister lid 50 is designed somewhat similarly to canister lid 8, and includes a patient port 54, a suction port 56 and a spout 58. The canister lid 50 may be sealably secured on top of a canister, such as canister 6, and will serve the same function as canister lid 8.

A cylinder 59 depends downwardly from the interior surface of lid 50, and a support ring 60 is inserted to frictionally engage the interior walls of cylinder 59. A plurality of fingers 62 extend downwardly and inwardly from the support ring 60, and a tubular plunger guide 64 depends downwardly from the lower ends of the fingers 62.

The soft rubber plunger 42 is mounted within the plunger guide 64. In the preferred embodiment, both plunger 42 and plunger guide 64 are cylindrical, and a silicone lubricant may be used between the plunger 42 and the plunger guide 64 to enhance the sliding motion of the plunger within the plunger guide. As previously described, the plunger 42 is preferably made from a silicon rubber, and if a silicone rubber is used, it is not usually necessary to use a silicone lubricant.

Still referring to FIG. 4, it will be appreciated that the disc 44 integrally formed on the top of plunger 42 has a diameter greater than the diameter of either plunger 42 or the interior diameter of plunger guide 64. Thus, when the fluid 16 is at a level below the level of the shut off valve 52, the plunger 42 slides downwardly in the plunger guide 64 until the disc 44 engages the fingers 62 and top of plunger guide 64 to limit the downward motion of plunger 42.

The lower end of plunger guide 64 includes an aperture 66 for allowing fluid and air to enter the plunger guide. When the fluid 16 rises to the level of the lower end of plunger guide 64, fluid begins to enter into the plunger guide through the aperture 66 as the fluid level rises. Because of the vertical disposition of plunger 42 and the fact that plunger 42 is substantially airtight, air is trapped within the plunger 42, and as the fluid 16 rises inside the plunger guide 64, the plunger 42 floats and slides upwardly. When the fluid 16 reaches a predetermined level generally indicated by line 68, the plunger will be forced against the lid 50 and the suction port 56. As indicated by dotted line 42', the disc 44 sealably engages the lid 50 to cover and block the suction port 56, thereby, preventing a vacuum from being created inside the canister.

Still referring to FIG. 4, the interior walls 70 of the suction port 56 are tapered such that the opening 72 at the top of suction port 56 is larger than the opening 74 at the bottom of the suction port. It will be appreciated that by providing a small opening 74 in the lid 50 above the disc 44, the danger of misalignment between the disc 44 and the opening 74 is diminished. Ideally, the opening 74 is aligned with the plunger 42 so that the opening 74 is centered with respect to the disc 44. However, if the plunger 42 is inadvertently skewed slightly out of alignment with the opening 74, the disc 44 is sufficiently large with respect to the small opening 74 to insure that the opening is still completely covered and blocked by the disc 44 when the fluid 16 rises the predetermined level indicated by dotted line 68.

Figure 5:
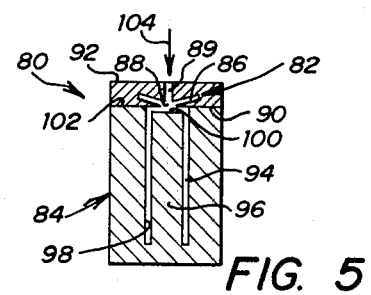
FIG. 5 is a cross section of a composite die for injection molding of the soft rubber plunger with a concave disc integrally formed on one end of the plunger.

Referring now to FIG. 5, there is shown a composite mold for forming a plunger 42 with an integrally formed disc 44. It will be appreciated that one of the advantages of using an integrally formed plunger 42 and disc 44 is that manufacturing may be accomplished by injection molding techniques such as illustrated in FIG. 5. The composite die 80 is formed from a disc die 82 in combination with a plunger die 84. The disc die 82 includes an upwardly facing, concave, disc shaped cavity 86 with an opening 88 extending from the center of the disc cavity 86 to the lower surface 90 of the disc die 82. Also, a bore 89 extends upwardly from the center of the disc shaped cavity 86 through the top surface 92 of the disc die 82. The plunger die 84 includes an annular cylindrical plunger cavity 94 for molding the plunger 42. The plunger cavity 94 is formed by a solid cylinder 96 extending upwardly through a cylindrical passage way 98 in the plunger die 84. The solid cylinder 96 is equidistantly spaced from the cylindrical passage way 98, and the top surface 100 of the solid cylinder 96 is spaced downwardly from the plane formed by the top surface 102 of the plunger die 84 so that the plunger cavity 94 is a cylinder having a disc shaped closed end adjacent surface 100.

To mold the plunger 42 and disc 44, the disc die 82 is positioned on the plunger die 84 as previously described to form the composite die 80 as shown in FIG. 5. Preferably, a silicone rubber is then injected through the bore 89 as symbolically illustrated by arrow 104. The injected rubber travels through the bore 89, through the center opening 88 and into the plunger cavity 94 and the disc shaped cavity 86. The rubber is then allowed to harden to a soft flexible state.

Figure 6:
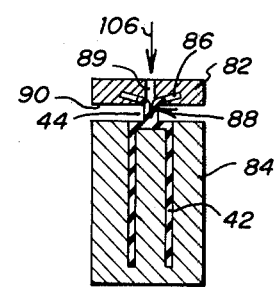
FIG. 6 is a partial cross section of the composite die showing the concave disc being removed from the disc die with air being injected into a bore in the top of the disc die.

Referring now to FIG. 6, there is shown the plunger 42 and the disc 44 in the process of being removed from the disc die 82 after the plunger and the disc have hardened to a soft flexible state. To remove the disc 44 from the disc cavity 86, the disc die 82 is moved upwardly away from the plunger die 84 while air is simultaneously injected into the bore 89 as indicated by the arrow 106. The disc 44 then elastically deforms and is simultaneoulsy blown and pulled through the opening 88 in the lower surface 90 of the disc die 82. The injection of air through bore 89 facilitates the removal of the disc 44 by eliminating excessive concentrated strain on the disc 44 during removal from the disc die 82. Finally, the plunger 42 is removed from the plunger die 84.

Although particular embodiments of the present invention have been described in the foregoing detailed description, it will be understood that the invention is capable of numerous rearrangements, modifications and substitutions of parts without departing from the spirit of the invention.

What is claimed is:

1. A composite die for forming a cylindrical hollow plunger having a concave disc integrally formed on one end of the plunger, comprising:
   a plunger die having an annular cylindrical cavity formed therein for molding a cylindrical hollow plunger having a closed end;
   a disc die for being positioned adjacent said plunger die to form the composite die, said disc die having a concave disc shaped cavity formed therein facing away from said plunger die and adjacent to said closed end, with an opening formed at the center of said disc shaped cavity and positioned over the center of said closed end of said annular cylindrical cavity;
   a bore means extending from the center of said disc shaped cavity to said closed end of said disc die for injecting rubber into said disc die and plunger die and for injecting air into said disc die to facilitate removal of the rubber disc formed therein; and
   means for moving said disc die and said plunger die away from one another while injecting air through said bore to facilitate removal of the rubber disc formed within said disc die.

* * * * *